United States Patent [19]

Provonchee et al.

[11] Patent Number: 4,774,093

[45] Date of Patent: Sep. 27, 1988

[54] POLYSACCHARIDE COMPOSITIONS, PREPARATION AND USES

[75] Inventors: Richard B. Provonchee, Camden; Donald W. Renn, Glen Cove, both of Me.

[73] Assignee: FMC Corporation, Philadelphia, Pa.

[21] Appl. No.: 748,521

[22] Filed: Jun. 25, 1985

[51] Int. Cl.$^4$ .................. C08L 3/02; C08B 37/00; B01J 13/00

[52] U.S. Cl. .................. 424/493; 106/205; 106/208; 351/160 R; 351/160 H; 252/315.3; 424/492; 424/496; 424/500; 536/1.1; 536/4.1; 536/115; 536/123; 536/124

[58] Field of Search .................. 252/315.3; 106/205, 106/208; 351/160 R, 160 H; 424/492, 493, 496, 500; 536/1.1, 4.1, 115, 123, 124

[56] References Cited

U.S. PATENT DOCUMENTS

| | | | |
|---|---|---|---|
| 3,754,925 | 8/1973 | Kimura et al. | 252/315.3 |
| 3,822,250 | 7/1974 | Kimura et al. | 252/315.3 |
| 3,899,480 | 8/1975 | Kimura et al. | 264/186 |
| 4,012,333 | 3/1977 | Towle | 252/315.3 |
| 4,264,155 | 4/1981 | Miyata | 351/160 H |
| 4,352,883 | 10/1982 | Lim | 424/496 |
| 4,430,322 | 2/1984 | Stoudt et al. | 536/123 |
| 4,447,562 | 5/1984 | Ivani | 351/160 R |
| 4,454,315 | 6/1984 | Sasaki et al. | 536/1.1 |
| 4,493,894 | 1/1985 | Miyashiro et al. | 435/101 |
| 4,514,318 | 4/1985 | Rodriguez | 252/315.3 |
| 4,529,797 | 7/1985 | Peik et al. | 536/1.1 |
| 4,567,140 | 1/1986 | Voelskow et al. | 252/315.3 |

FOREIGN PATENT DOCUMENTS 1500456 2/1978 United Kingdom .
2090847 7/1982 United Kingdom .

OTHER PUBLICATIONS

ACS Symposium Series No. 45, pp. 265–283 (published 1977).
Progress in Industrial Microbiology, vol. 18, pp. 201–229, published 1983.
Agric. Biol. Chem., 41(7), pp. 1315–1316 (1977).
Polysaccharides in Food, 18, pp. 283–300 (1979).

*Primary Examiner*—Ronald W. Griffin
*Attorney, Agent, or Firm*—Patrick C. Baker; Christopher Egolf

[57] ABSTRACT

Novel beta-1,3-glucan polysaccharide gels characterized by (a) coherent, uniform, non-particulate structure, and (b) substantially uniform pH throughout. The gels are prepared by dissolving a beta-1,3-glucan polysaccharide in an aqueous alkaline medium at a temperature of about 55° C. or below and while maintaining the solution at a temperature of at least 50° C., adjusting the pH to 10.5 or lower, followed by cooling below about 40° C. or heating above 50° C. The gels formed by cooling are reversible whereas the gels formed by heating are thermally irreversible. The gels are useful for supporting, separating, transforming or treating biological materials, as carriers for pharmaceuticals, as coatings for biological materials, in food products, and can be shaped to form disposable contact lenses.

40 Claims, No Drawings

POLYSACCHARIDE COMPOSITIONS, PREPARATION AND USES

BACKGROUND OF THE INVENTION

This invention relates to polysaccharide compositions of the gel-forming beta-1,3-glucan type and to methods of preparing and using solutions and gels of the polysaccharides. The novel gels of the invention provide added benefits in established fields and open up a myriad of new applications for the polysaccharides in foods, industrial products and processes, and in a broad spectrum of cosmetics, pharmaceutical and biomedical applications.

The beta-1,3-glucan polysaccharides are unique because they are the only known polysaccharides, other than agarose, which not only are neutral but also form nearly transparent, relatively firm hydrogels at low concentrations. These polysaccharides are exo-3-glucan polymers composed almost exclusively of beta-(1, 3)-glucosidic linkages. The beta-1,3-glucan polysaccharides widely distributed in nature as components of yeasts (cell walls), land and sea plants, and seeds (also as cell walls), and can be biologically produced, for example by microbial fermentation. Microorganisms which produce the beta-1,3-glucans include bacteria of the genera Alcaligenes, Agrobacterium and Streptococcus of which the species *Alcaligenes faecalis, Agrobacterium radiobacter, Agrobacterium rhizogenes* and *Streptococcus mutans,* including variants and mutations thereof, are the most widely known. The bacterially produced beta-1,3-glucan polysaccharides are also known as curdlans, Takeda polysaccharide 13140, scleroglucans, succinoglucans, schizophyllans, pachymans (from the fungus *Poria cocos*), paramylons and by other designations.

The beta-1,3-glucan polysaccharides are extensively described in the patent and technical literature, such as U.S. Pat. Nos. 3,754,925 and 3,822,250; "Production, Properties, And Application of Curdlan", T. Harada, in *Extracellular Microbial Polysaccharides,* ACS Symposium Series No. 45, American Chemical Society, Washington, D.C., 1977, 265–283 (1977); and "Curdlan: Its Properties And Production In Batch And Continuous Fermentations", K. R. Philipps and H. G. Lawford, *Progress in Industrial Microbiology,* ed. M. E. Bushell, 18, 201–229 (1983), Elsevier Scientific Publishing (Amsterdam). The last article and U.K. patent application No. 2090847A, published July 21, 1982, describe a two-stage continuous process for producing curdlan-type polysaccharides from microorganisms such as *Alcaligenes faecalis* var. *myxogenes* (ATCC 31749 and ATCC 31750). The curdlan-type polysaccharides are preferred for use in the present invention.

Despite the many studies devoted to production and uses of the beta-1,3-glucan polysaccharides, these materials have not been commercialized. A primary reason for this is the lack of a convenient and economical method for forming gels. Known gel-forming processes include (1) heating a swollen, aqueous paste of the polysaccharide powder, resulting in a semi-continuous, particulate gel; (2) heating an aqueous suspension of the polysaccharide; (3) acidifying an alkaline solution of the polysaccharide by dripping the solution into aqueous hydrogen chloride (U.S. Pat. No. 3,899,480), by treating with a slow release acid encapsulated in a polymeric matrix (British Pat. No. 1,500,456) or by treating with acid anhydride vapor such as gaseous carbon dioxide (U.S. Pat. No. 4,012,333); (4) diluting with water a solution of the polysaccharide in an organic solvent such as dimethyl sulfoxide; and (5) dialyzing alkaline solutions against various solutions.

All of these methods are unduly cumbersome and/or uneconomical on a commercial scale. Moreover, they do not provide the good control over polysaccharide concentration, gel structure and ionic environment throughout the gel, which are required in many applications of the gels, particularly in the treatment of sensitive biological materials.

SUMMARY OF THE INVENTION

One aspect of the invention is a novel beta-1,3-glucan polysaccharide gel, characterized by (a) coherent, uniform, non-particulate structure as determined visually and by continuous, uniform staining with Aniline Blue, and (b) substantially uniform pH throughout the gel structure immediately upon formation of the gel.

By "coherent" in this specification is meant a continuous, cohesive appearance, free of undissolved particles (although microscopic fibrils may be present) and swollen masses, both to the unaided eye and when stained with Aniline Blue. In contrast, prior beta-1,3-glucan polysaccharide gels, such as those prepared from suspensions, as in U.S. Pat. Nos. 3,754,925 and 3,822,250, are characterized by phase discontinuity and pockets of swollen, undissolved particles, as made more evident by mottling high-lighted by Aniline Blue staining. The coherency reflects more homogeneous polysaccharide concentration and structure, thereby enhancing the usefulness of the gels as media for supporting, separating, transforming or treating biological materials.

The substantially uniform pH throughout the gels of the invention immediately upon formation contrasts wih the character of the gels prepared by the method of U.S. Pat. No. 4,012,333 to Towle. In Towle, an alkaline solution of a beta-1,3-glucan-type polysaccharide is gelled by exposure to an atmosphere of a gaseous acid anhydride such as carbon dioxide. The gelling technique requires slow diffusion of the gaseous acid anhydride through the polysaccharide solution, with the result that a pH gradient (for example, from about 4 to 8) occurs in the gel. An adverse consequence of the need to hold a solution at an alkaline pH is that the gels cannot be used to support materials such as cells, enzymes, antibodies, and the like, which are sensitive to alkaline pH or to a pH range.

In another aspect of the invention, a convenient low cost method (hereinafter sometimes called the "Critical Temperature Neutralization" or "CTN" method) has been found for preparing solutions and gels of the beta-1,3-glucan polysaccharides based upon the discovery of a narrow temperature range where neutralization or reduction of the pH of an alkaline solution of the polysaccharides to 10.5 or lower does not immediately induce gellation. However, the solution, once formed in the critical temperature range and having a pH of 10.5 or lower, can be conveniently gelled either by cooling to form a thermally reversible ("cold set" or "low set") gel, or by further heating to form a thermally irreversible ("heat set" or "high set") gel.

In the CTN method for preparing solutions and gels of the invention, a suitable beta-1,3-glucan polysaccharide is dissolved in an aqueous alkaline medium (pH over 10.5) at a temperature at or below about 55° C. The resulting solution is then heated, if necessary, to the critical temperature (at least 50° C. but lower than a temperature which will cause decomposition) and the pH of the solution is adjusted to 10.5 or lower by addition of an acid. As indicated, the resulting substantially neutralized solution may then be gelled quickly to a thermally irreversible condition by further heating above 50° C. or to a thermally reversible state by cooling. In either case the resulting novel gels are homogeneous and have precisely known polysaccharide content, pH and other characterisitcs which lead to new uses as well as enhanced benefits in established applications.

In still other aspects of the invention, the novel gels provide superior media in methods for supporting, separating, transforming (culturing, cleaving, cloning, etc.) or treating (including purifying) biological materials, such as electrophoresis, electroimmunoassay, immunoelectrophoresis, immunodiffusion, immunoprecipitation, cell culturing and cloning, nucleic acid digestion, enzyme immobilization, isoelectric focusing, affinity chromatography, gel filtration, specimen immobilization, and a host of other biotechnical applications. In these well-known techniques, biological material is incorporated into (for example, by diffusion after gelation) or placed in contact with a gel medium for examination, assay, culturing or other purpose. The gels are also useful in foods, as medicinal films, as tabletting materials and slow-release coatings for pharmaceuticals, in heat resistant toothpaste and a variety of fiber and film products, and for the manufacture of disposable contact lenses. Beads and granules are also conveniently prepared from the gel-forming solutions of the invention, in the manner described in U.S. Pat. No. 4,493,894.

DETAILED DESCRIPTION

The coherent character of the gels of the invention is normally observable with the unaided eye. In borderline cases, however, or if it is desired to dramatically demonstrate this property, the gel can be stained with Aniline Blue utilizing, for example, the technique of Natanishi et al, J. Gen. Appl. Microbiol. 22, 1-11 (1976). The gels of the invention stain continuously and completely, whereas prior polysaccharide gels stain to a discontinuous, striated or mottled appearance, indicating the presence of non-uniform polysaccharide concentration, sometimes visually apparent as particles more or less swollen.

The uniform polysaccharide concentration of the gels of the invention provides significant benefits. For example, the migration of molecules through the gel will be more controlled since the pores of the gel are more regularly spaced. Electrophoretic and other methods for separation of biological molecules are therefore enhanced.

The pH gradient, if any, in a polysaccharide gel is conveniently determined potentiometrically or by adding a universal indicator to the alkaline gel-forming solution and then inducing gellation. When a polysaccharide gel prepared by the acid anhydride treatment of Towle (U.S. Pat. No. 4,012,333) is sectioned, a pH gradient is evident from the different colors among or within the sections. All sections of the gels of the invention, in contrast, have only a single color. As indicated, the ability to control the pH in a gel, particularly if a gel can be prepared having a neutral or acid pH, is vital when it is desired to use the gel as a medium for alkali-sensitive biological materials. An alkaline pH, even in only a portion of the gel, will destroy that part of a biological material in contact therewith or will otherwise impair the efficiency of the treatment for which the gel is intended.

In preparing solutions of the polysaccharides according to the "Critical Temperature Neutralization" method of the invention, the starting material is a natural or microbially produced, neutral beta-1,3-glucan polysaccharide which is normally insoluble in neutral aqueous medium but soluble in alkaline aqueous medium. The starting material preferably is the dry, curdlan-type polysaccharide separated from a culturing medium by known methods, such as described in U.S. Pat. No. 3,822,250 or U.K. published patent application No. 2090847A cited above. Such material is normally solid or powdery and forms an aqueous suspension or slurry when dispersed in aqueous medium below pH 10.5. The starting material may also be a cold-set (reversible) gel prepared by prior art methods.

The polysaccharide material may be directly dissolved in an aqueous alkaline medium in amounts of about 0.1 to about 25 wt. %, preferably about 0.5 to about 5.0 wt. %, or an alkali may be added to an aqueous suspension or slurry containing about the same amount of the polysaccharide, to form the required solution, in both cases while maintaining the temperature of the aqueous mixture at or below about 55° C., for example, in a range of about 10° C. to 55° C. Relatively minor amounts of alkaline material may be used for the dissolution, for example, from about 0.05 to 10% by weight of NaOH, KOH, NH$_4$OH, an organic base such as an alkyl, aryl or aralkyl amine, a hydroxyl substituted amine, or any mixtures thereof. When the material is thus fully dissolved, the resulting solution will have a pH over 10.5, for example, about 12.

If not already at an elevated temperature, the resulting solution is heated to at least 50° C. but with care taken to avoid raising the temperature to the point where the polysaccharide will decompose. A preferred temperature is in the range of from about 50° C. to about 60° C. but temperatures in individual cases will depend upon the particular polysaccharide material being processed. A surprising and unexpected feature of the invention is that the alkaline solution can be neutralized (described below) and held in this narrow temperature range without immediate gellation. This discovery permits manipulation of the polysaccharide so that reversible or irreversible high strength gels can be formed from the solution in a convenient and economical manner, without resort to preparation of suspensions or other complex treatments.

While maintaining the alkaline solution at the elevated temperature the pH is adjusted to 10.5 or less, preferably to about 7 but optionally as low as pH 1, usually by the addition of an acid. (This step is sometimes referred to in this specification as a "neutralization" or as an "acidification." When used, these terms generally indicate addition of an acid to offset the high alkalinity of the solution by reducing the pH of the solution to 10.5 or less, or to a neutral or acidic condition). Either organic or mineral acids or any mixtures thereof may be used for the pH adjustment including citric, acetic and other carboxylic acids, mineral acids such as hydrochloric, nitric and phosphoric acid, or an acid generating material such as gamma butyrolactone. The resulting solution may be buffered, if desired, to stabilize it for particular applications.

As thus prepared the solution (optionally buffered) is ready for gellation either to a thermally irreversible state by heating above 50° C., or to a reversible state by cooling, usually below about 40° C. For the bacterially produced beta-1,3-glucans, gellation to the thermally irreversible state readily occurs upon heating of the neutralized solutions to the range of about 80° C. to 90° C. Temperatures which will cause melting of the gels, possibly accompanied by decomposition, should be avoided. In the case of the curdlans, melting temperature is about 140°-160° C., depending on the degree of polymerization. As with any gelling polysaccharide, it will be understood that with the passage of time the solutions of the invention wil gel. However, gelation can now be conveniently controlled, and even reversed if a cold set gel, based on the discovery of the critical temperature range in which gelling of the neutralized solutions will not occur for a reasonable period.

The beta-1,3-glucan gels can be stored as is, with or without additives such as described in U.S. Pat. No. 3,527,712, or can be partially or completely dried and later rehydrated since they are remarkably stable to autoclaving and freeze-thaw cycling.

The gels, whether of the high temperature or low temperature type, are firm, coherent and have good gel strength (of the order of 65-70 g/cm$^2$ for a 1% (w/v) polysaccharide (curdlan-type) concentration as measured by a Marine Colloids Gel Tester). Other beta-1,3-glucan polysaccharides provide similar results.

The following examples will further illustrate the invention without necessarily limiting the spirit and scope thereof, it being understood that the invention is entitled to the full scope and range of equivalents indicated in the appended claims.

EXAMPLE 1

A powdery beta-1,3-glucan sample (2.0 g), supplied by Takeda Chemical Industries Ltd. and identified as Takeda Polysaccharide 13140, is dissolved in 200 ml of a 0.05N sodium hydroxide solution. The flask containing the solution is then placed on a 55° C. water bath and allowed to equilibrate. While agitating and maintaining the temperature at 55° C., phosphoric acid (2 ml, 5N) is added to the solution. The resulting neutralized solution remains liquid and is then divided approximately equally between two gelling dishes. One dish (Sample A) is placed in a water bath at 85° C. for one hour and the other dish (Sample B) is allowed to cool to room temperature (about 22° C.). Each solution gels within 10 minutes. After an hour at their respective temperatures, the two gel samples are refrigerated at about 4° C. for two hours. After the refrigeration, gel strength measurements (break force) are made on the two samples using a Marine Colloids Division, FMC Corporation, Gel Tester. The Sample A gel exhibits a gel strength of 68 g/cm$^2$; the Sample B gel has a gel strength of 65 g/cm$^2$. Sample A on being warmed to 55° C. does not change in appearance. Sample B, however, liquefies at 55° C. but again sets upon heating above 80° C. or cooling to room temperature.

Each gel sample when stained according to the procedure of Nakanishi et al, J. Gen. Appl. Microbiol. 22, 1-11 (1976), using 0.02% Aniline Blue (Sigma) in 0.1M sodium phosphate buffer (pH 7) exhibits a continuous coloration, without striation, mottling or other evidence of particles or localized polysaccharide concentration, as is the case when the gels are prepared from suspensions as described in U.S. Pat. Nos. 3,754,925 and 3,822,250. Moreover, the gels of the invention prepared in accordance with this example have smooth surfaces and when formed from solutions containing Universal Indicator and thereafter sectioned, exhibit a single color throughout the sections, demonstrating a uniform pH throughout. Gels prepared by the Towle method (U.S. Pat. No. 4,012,333) in contrast have rough, orange peel-like surfaces and light refracting striations within the gels, indicating concentration differentials. Moreover, the Towle gels, when prepared from solutions containing Universal Indicator and sectioned, exhibit various colors within specific sections as well as between the sections, showing that the gels, as formed, characteristically have a pH gradient.

EXAMPLE 2

The procedure of Example 1 is repeated in all essential respects except for substitution of acetic acid (glacial) for the phosphoric acid. Again, the solutions do not gel upon addition of the acid at 55° C. When heated further and/or cooled as in Example 1, firm, coherent, high strength gels form. The gel sample heated above 80° C. is irreversible to temperature variations. The sample which is gelled by cooling from 55° C. to room temperature liquefies upon reheating to 55° C. but can be reversibly reset by cooling or irreversibly reset by heating above 80° C.

EXAMPLE 3

This example illustrates the substantially uniform pH exhibited throughout gels of the invention as contrasted with the pH gradient of the gel described in Example 5 of U.S. Pat. No. 4,012,333-Towle, which ranged from pH 6.9 at the top of the gel to pH 7.4 at the bottom of the gel.

A 5% solution of polysaccharide in 0.2% NaOH is heated in a water bath to a temperature of 55° C. While agitating and maintaining the temperature at 55° C., sufficient phosphoric acid (10N) is added to the solution to bring the pH to between 3 and 4. The solution is poured into a cylindrical container with an inner diameter of about 1.5 cm to a depth of about 13 cm. The solution forms a firm gel after sitting for about 10 minutes at room temperature. After several hours, the gel is removed from the cylinder and the pH measured potentiometrically. At the top of the gel the pH is 3.34, and at the bottom it is 3.31. Since these values are within experimental error, they are substantially the same, indicating that the pH is uniform.

USES OF THE POLYSACCHARIDE COMPOSITIONS

The following sections A through D and H illustrate modes of supporting, separating, transforming or treating biological materials utilizing the polysaccharide solutions and gels of the invention. The remaining sections illustrate other uses. Equivalent uses will be immediately apparent to those skilled in the art.

A. Electrophoresis Gel Media

1. Serum electrophoresis

A 1% neutralized solution of Takeda Polysaccharide 13140 is prepared as described in Example 1. Barbital buffer (about 0.04N) is added to the solution to maintain the pH at 8.2. The resulting solution at about 50° C. is poured onto 4"×5" sheets of FMC Corporation Gel-Bond® film and allowed to cool at about 22° C., whereupon gelling occurs. Serum samples (2 microliters each) are deposited in precut wells, and using a standard power supply and electrophoresis chamber with blotting paper wicks and 0.04N (pH 8.2) barbital buffer in the reservoirs, electrophoresis is carried out at 14 mA for 3 hours. The resulting separation is visualized by Coomassie Blue protein stain. Little, if any, cathodal migration is observed, and the separation pattern is similar to that expected for an agarose gel of like concentration. When lactic dehydrogenase substrate reagents are used to visualize a run, satisfactory LDH patterns are observed. Use of a curdlan polysaccharide obtained from Hercules Corporation or George Weston Limited gives similar results, and clarified locust bean gum, starch or other hydrocolloids can be added to the solutions to control gel syneresis.

2. RNA, DNA electrophoresis

Cold-set coherent gels are prepared as described in the serum electrophoresis illustration above except for a Tris buffer (50 mM) in place of the barbital. Five microliters of a standard restriction endonuclease fragmented λ bacteriophage solution is deposited in each of three precut wells. An electric potential is applied across the gel, sufficient for separation. Following this separation, one lane is visualized using ethidium bromide. Areas corresponding to DNA fragments are cut from the gel and the DNA recovered by adding sufficient 0.1N NaOH to dissolve the gel. Following neutralization with mixing, to precipitate the polysaccharide, and centrifugation, the supernatant is found to contain the recovered DNA. Similar procedures can be used for RNA.

3. Denaturing solvent electrophoresis

Certain electrophoretic separations, such as those necessary to detect DNA single-point mutations, require gel media containing concentrations of formamide, urea, and other such denaturing agents, that preclude formation of agarose gels. As described in Proc. Natl. Acad. Sci. USA, 89, 1579–1583 (March 1983), chemically cross-linked gels, such as polyacrylamide, can be used, but these considerably restrict the size of molecules which can be separated.

To determine if a 1% beta-1,3 glucan gel will form in the presence of high concentrations of denaturing agents, the following gels are prepared by forming polysaccharide solutions essentially as described in Example 1, adding urea and/or formamide, and then heating or cooling, also as described in Example 1.

(a) 0.87% Takeda polysaccharide 13140 solution 5.2M urea (b) 1.0% Takeda polysaccharide 13140 solution 9M urea (c) 1.0% Takeda polysaccharide 13140 solutions 9M urea 25% formamide (d) 1.0% Takeda polysaccharide 13140 solution 9M lithium bromide All four compositions form firm, coherent gels with little syneresis, thus demonstrating good gel forming ability in the presence of the denaturants. Proteins and nucleic acid fragments can be separated in these gels using standard electrophoretic conditions.

4. Gels for isoelectric focusing (IEF)

Because of the very low to no electroendosmosis observed with gels prepared with Takeda polysaccharide 13140 or other curdlan-type polysaccharides, prepared by the method of Example 1, the addition of appropriate ampholytes to the neutralized solutions before they gel provide excellent IEF gel media. For example, a gel suitable for IEF is prepared using 5 ml of a 2% solution of Takeda polysaccharide in 0.2N NaOH heated to 55° C. and neutralized with 5M $H_3PO_4$. An equal volume of water at 55° C. containing 0.63 mL of ampholyte (Marine Colloids Division, FMC Corporation) and 1 g of d-sorbitol is added. The mixture is then quickly and evenly spread on a 11×12.5 cm sheet of GelBond ® plastic film and allowed to gel. Solutions of standard protein pI markers are applied, using an application mask. These are placed in a standard electrophoresis chamber with paper wicks connecting the plate to a 0.5M acetic acid anolyte and a 0.1 M NaOH catholyte. A 500-volt potential is applied for 90 minutes. Staining with Coomassie Blue shows that a discernible separation occurs.

B. Immunoprecipitation gel media

1. Immunodiffusion

A 1.5 mm thick film of 1% Takeda Polysaccharide 13140 gel, formed as described in Example 1, is prepared. Using a 2-mm diameter vacuum die, a central well surrounded by six outer wells, all spaced 2 mm apart, is cut. In the center well of this Ouchterlony immuno-diffusion pattern is placed 5 microliters of normal human serum with various rabbit antihuman serum protein fraction antisera in the surrounding wells, including IgA, IgG, IgM, albumin and alpha-1 anti-trypsin. All of the antisera, even the IgM, form visible precipitin lines after overnight incubation, showing that diffusion of as large a molecular species as IgM is not restricted by the 1% (w/v) glucan gel structure. In fact, the IgM-anti IgM precipitin lines appear midway between the wells.

2. Immunoelectrophoretic procedures

Gels prepared according to the Electrophoresis Gel Media procedure, A(1) above, are adapted to electroimmuno- diffusion and immunoelectrophoresis. Results similar to those in agarose controls are obtained. C. Microbiological media To 50 ml of a solution of 1% Takeda Polysaccharide 13140 in 0.06N NaOH, and heated to 60° C., is added 1.2 g trypticase soy nutrient medium components. The pH of this solution is adjusted to 7.0 and 15-ml portions are poured into 100 mm×10 mm petri dishes. These are allowed to gel to a thermoreversible state and one is autoclaved to form a heat-set gel. Both are then streaked with *E. coli* and *B. subtilis* and incubated. Satisfactory growth is observed for each. The heat-set microbiological media gel has particular value in that it can be used as a solid nutrient media base for culturing thermophilic microorganisms at temperatures of ≧90° C. where agar(ose) media would become fluid.

D. Beta-1,3-glucan gel particles as carriers for biologicals

Beads and other particles of the beta-1,3-glucans of the invention are prepared in accordance with the teachings of U.S. Pat. Nos. 4,143,201 and 4,493,894. The resulting beads are useful as carriers for immobilized enzymes and other biological materials in affinity chromatography, gel filtration, and other applications. Using the Critical Temperature Neutralization method of this invention, however, not only can the beads be produced and the applications cited in these patents be practiced more easily, but additional appplications are possible, such as microencapsulation, living cell encapsulation, formation of biodegradable therapeutic agent microcarriers, agglutination media, and immunoassay substrates. Most of these uses would not be possible where the initial solution contacting the reagents is highly alkaline.

E. Targeted release coatings or carrier media for pharmaceuticals

It is frequently desirable to transport drugs, which are unstable in stomach acids or react adversely with the stomach lining, through the stomach. Gels of beta-1,3-glucans serve this purpose by virtue of their acid insoluble, base soluble characteristics. Accordingly, it is now possible, as in Example 1, to prepare in one step a solution of beta-1,3-glucans for gelling in contact with a drug preparation. By appropriate selection of polysaccharide, thickness of the gel and concentration of drug in the gel, the thus-formulated pharmaceutical will have controlled release, e.g., slow-release, characteristics.

F. Edible gels

Human and animal foods based on coherent beta-1,3-glucan gels are more easily prepared (in accordance, for example, with the teachings of U.S. Pat. No. 3,822,250) with the solutions and gels of the invention such as those of Example 1.

G. Toothpaste

Heat-stable beta-1,3-glucan based gel toothpastes are conveniently prepared with neutralized solutions and gels of the invention by adding suitable amounts of abrasives, edible dyes, flavors and/or sweeteners, and other known dentrifice ingredients to a neutralized polysaccharide solution of Example 1 and cooling or heating to cause the solution to gel.

H. Gel coatings for biological materials

By preparing a 1% (w/v) solution of Takeda polysaccharide 13140 in 0.05N NaOH, heating to 55° C. and neutralizing with 5N $H_3PO_4$, seeds, embryos, plantlets and the like can be coated by dipping into the solution and rapidly cooling to gel. Drying is optional as is the addition of nutrients, humectants, hormones, and the like.

I. Disposable contact lenses

Using the method of Example 1 to prepare neutralized beta-1,3-glucan solutions, and using as is or including polymeric additives which can be later leached for increased porosity and therefore liquid and/or gas permeability, the solutions are poured into contact lens molds, and then heat-treated to form contact lenses. The lenses are sterilized by boiling. Illustrative of this process, 1 ml of the neutralized solution described in Example 1 (at 55° C.) is placed in one of the hemispherical wells of a multiwell spot plate at 50° C. The spot plate containing the solution is heated to 100° C. for 10 minutes under high humidity conditions to retard evaporation. The resulting gel simulates a contact lens and can be boiled for sterilization. If agarose or another boiling water leachable hydrocolloid is added during solution preparation, a more porous final product is obtained. Upon drying, at least partial rehydration is possible by placing the gelled product in water.

We claim:

1. A beta-1,3-glucan polysaccharide gel characterized by (a) coherent, uniform, non-particulate structure, and (b) a substantially uniform pH throughout.

2. The gel of claim 1 wherein the polysaccharide is biologically produced.

3. The gel of claim 1 wherein the polysaccharide is produced by a microorganism of the genus Alcaligenes or Agrobacterium.

4. The gel of claim 1 wherein the polysaccharide is produced by the microorganism *Alcaligenes faecalis var. myxogenes.*

5. A method of preparing an aqueous polysaccharide solution capable upon cooling below about 40° C. of forming a reversible, high strength gel and capable upon being heated above about 50° C. of forming a thermally irreversible, high strength gel, said gel having a coherent, uniform, non-particulate structure and a substantially uniform pH throughout, which method comprises:
 (a) providing a beta-1,3-glucan polysaccharide normally insoluble in neutral aqueous medium but soluble in alkaline aqueous medium;
 (b) dissolving the polysaccharide in an aqueous alkaline medium at a temperature of about 55° C. or below to provide a solution thereof; and
 (c) while maintaining the solution at a temperature of at least 50° C. but lower than the decomposition temperature of the polysaccharide, adjusting the pH of the solution to 10.5 or lower.

6. The method of claim 5 wherein the polysaccharide is biologically produced.

7. The method of claim 5 wherein the polysaccharide is produced by a microorganism of the genus Alcaligenes or Agrobacterium.

8. The method of claim 5 wherein the polysaccharide is produced by the microorganism *Alcaligenes faecalis var. myxogenes.*

9. The method of claim 5 wherein the pH of the solution is adjusted by the addition of an organic acid.

10. The method of claim 9 wherein the organic acid is acetic acid.

11. The method of claim 5 wherein the solution is neutralized by the addition of a mineral acid.

12. The method of claim 11 wherein the mineral acid is phosphoric acid.

13. The polysaccharide solution prepared by the method of claim 5.

14. The polysaccharide solution prepared by the method of claim 6.

15. The polysaccharide solution prepared by the method of claim 7.

16. The polysaccharide solution prepared by the method of claim 8.

17. A method of preparing a reversible, high strength gel of a beta-1,3-glucan polysaccharide, which comprises cooling below about 40° C. the polysaccharide solution of claim 13.

18. A method of preparing a reversible, high strength gel of a beta-1,3-glucan polysaccharide, which comprises cooling below about 40° C. the polysaccharide solution of claim 14.

19. A method of preparing a reversible, high strength gel of a beta-1,3-glucan polysaccharide, which comprises cooling below about 40° C. the polysaccharide solution of claim 15.

20. A method of preparing a reversible, high strength gel of a beta-1,3-glucan polysaccharide, which comprises cooling below about 40° C. the polysaccharide solution of claim 16.

21. The reversible polysaccharide gel prepared by the method of claim 17.

22. The reversible polysaccharide gel prepared by the method of claim 18.

23. The reversible polysaccharide gel prepared by the method of claim 19.

24. The reversible polysaccharide gel prepared by the method of claim 20.

25. A method of preparing a thermally irreversible, high strength gel of a beta-1,3-glucan polysaccharide, which comprises heating above 50° C. the polysaccharide solution of claim 13.

26. A method of preparing a thermally irreversible, high strength gel of a beta-1,3-glucan polysaccharide, which comprises heating above 50° C. the polysaccharide solution of claim 14.

27. A method of preparing a thermally irreversible, high strength gel of a beta-1,3-glucan polysaccharide, which comprises heating about 50° C. the polysaccharide solution of claim 15.

28. A method of preparing a thermally irreversible, high strength gel of a beta-1,3-glucan polysaccharide, which comprises heating above 50° C. the polysaccharide solution of claim 16.

29. The thermally irreversible polysaccharide gel prepared by the method of claim 25.

30. The thermally irreversible polysaccharide gel prepared by the method of claim 26.

31. The thermally irreversible polysaccharide gel prepared by the method of claim 27.

32. The thermally irreversible polysaccharide gel prepared by the method of claim 28.

33. In a method for supporting, separating, transforming or treating biological materials wherein a biological material is incorporated into or placed in contact with a gel medium, the improvement which comprises utilizing as the gel medium the beta-1,3-glucan polysaccharide gel of claim 1.

34. In a method for supporting, separating, transforming or treating biological materials wherein a biological material is incorporated into or placed in contact with a gel medium, the improvement which comprises utilizing as the gel medium the beta-1,3-glucan polysaccharide gel of claim 17.

35. In a method for supporting, separating, transforming or treating biological materials wherein a biological material is incorporated into or placed in contact with a gel medium, the improvement which comprises utilizing as the gel medium the beta-1,3-glucan polysaccharide gel of claim 29.

36. In a method for preparing a gel medium containing a biological material wherein the biological material is incorporated into the gel by dispersing the biological material into a precursor gel-forming solution and thereafter gelling the resulting dispersion by cooling below about 40° C. or heating above about 50° C., the improvement which comprises utilizing as the gel-forming solution the solution of claim 5.

37. A biological product comprising a biological material and a carrier therefor, said carrier comprising a gel of claim 1 in particulate form.

38. A pharmaceutical composition comprising a drug and a carrier therefor, said carrier comprising a gel of claim 1.

39. A biological material having a coating of the gel of claim 1.

40. A disposable contact lens comprising a contact lens shaped gel of claim 1.

* * * * *